(12) United States Patent
Rifkin

(10) Patent No.: US 6,491,954 B2
(45) Date of Patent: Dec. 10, 2002

(54) ANTI-SNORING COMPOSITION

(75) Inventor: Kenneth Rifkin, Portland, OR (US)

(73) Assignee: Green Pharmaceuticals, Inc., Wilsonville, OR (US)

( * ) Notice: Subject to any disclaimer, the term of this patent is extended or adjusted under 35 U.S.C. 154(b) by 0 days.

(21) Appl. No.: 10/029,632

(22) Filed: Oct. 24, 2001

(65) Prior Publication Data

US 2002/0076448 A1 Jun. 20, 2002

Related U.S. Application Data

(63) Continuation-in-part of application No. 09/746,803, filed on Dec. 20, 2000, now abandoned.

(51) Int. Cl.⁷ .................. A61K 33/24; A61K 35/78; A01N 59/16; A01N 65/00
(52) U.S. Cl. .................. 424/656; 424/725; 424/726; 424/769; 424/776; 424/779
(58) Field of Search .................. 424/769, 725, 424/656, 726, 779, 776

(56) References Cited

PUBLICATIONS

"PDR for Herbal Medicines" "*Ephedra Sinica*"; "*Hydrastis Canadensis*" and "*Teucrium Chamaedrys*" pp. 826–827, 903, 1177–1179 First Edition Medical Economics Company Montvale, N.J. 1998.*
Johnson "CRC Ethnobotany Desk Reference" *Ephedra Vulgaris* No. 9747 p. 303 CRC Press 1999.*
Derwent Computer Abstract 2000–326965 Sergeeva O Yu RU2131738 Jun. 20, 1999.*
Derwent Computer Abstract 2000–363087 Sephtein et al RU2133123 Jul. 20, 1999.*
Derwent Computer Abstract 2000–254863 Sergeeva O Yu RU2124898 Jan. 20, 1999.*
Derwent Computer Abstract 1999–079835 Dobrescu RO113805 Nov. 30, 1998.*
Derwent Computer Abstract 1998–284435 Sergee RU2088221 Aug. 27, 1997.*
Castelman "The Healing Herbs" Ephedra pp. 158–160 Rodale Press Emmaus, Pa 1991.*

* cited by examiner

Primary Examiner—Herbert J. Lilling
(74) Attorney, Agent, or Firm—Chernoff, Vilhauer, McClung & Stenzel, LLP

(57) ABSTRACT

An anti-snoring composition especially effective in the form of a throat spray is disclosed, the composition comprising an aqueous ethanolic solution of seven homeopathic ingredients.

10 Claims, No Drawings

ANTI-SNORING COMPOSITION

This is a continuation-in-part of application Ser. No. 09/746,803 filed Dec. 20, 2000 now abandoned.

BACKGROUND OF THE INVENTION

Snoring is a sleep disorder that can range from mild to severe in humans. Mild cases may result in no more than fitful sleep by the sufferer, while severe cases at the minimum cause disturbance of the sleep of others, and may result in insufficient inhalation of oxygen by the sufferer, apnea and, in extreme cases, death.

Many attempts have been made to devise remedies to alleviate the symptoms of snoring, ranging from surgery to a variety of medicaments. Although surgery has been proven to be somewhat effective, it is a radical and expensive approach that is subject to all the usual risks associated with surgery. There are a few effective drugs available for the treatment of the symptoms of snoring, but these are typically available only by way of prescription. There is therefore a need for an inexpensive non-prescription anti-snoring composition that is safe and effective. This need is fulfilled by the present invention, which is summarized and described in detail below.

BRIEF SUMMARY OF THE INVENTION

The invention comprises an anti-snoring composition made up of an aqueous ethanolic solution of seven active homeopathic ingredients, namely (i) Belladonna, (ii) *Ephedra vulgaris*, (iii) *Histamine hydrochloride*, (iv) *Hydrastis canadensis*, (v) *Potassium dichromate*, (vi) *Nux vomica* and (vii) *Teucrim marum*.

DETAILED DESCRIPTION OF PREFERRED EMBODIMENTS

According to the present invention the composition is made by combining equal parts by weight of eight aqueous ethanolic solutions of the aforementioned seven active homeopathic ingredients. Each ingredient is diluted in accordance with conventional homeopathic formulation procedures using an aqueous solution containing 20 vol % of 95 vol % ethanol.

Active ingredients (iii) (*Histamine hydrochloride*) and (v) (*Potassium dichromate*) are organic and inorganic chemicals, respectively, and are commercially available in 20 vol % aqueous ethanolic solutions from Boericke & Tafel, Inc. of Santa Rosa, Calif. The remainder of the active ingredients are all derived from plants as follows: (i) Belladonna—an alkaloid extracted from the entire plant from roots to flower of Deadly Nightshade plant, commercially available in 20 vol % aqueous ethanolic solutions from Boericke & Tafel; (ii) *Ephedra vulgaris*—a decongestant extracted from the stems and branches of the Ma huang or Mormon tea plant, commercially available in 20 vol % aqueous ethanolic solutions from Boericke & Tafel; (iv) *Hydrastis canadensis*—the active ingredient comprises three isoquinoline alkaloids extracted from the air-dried rhizome and roots of the herb Golden seal, commercially available in 20 vol % aqueous ethanolic solutions from Boericke & Tafel; (vi) *Nux vomica*—the active ingredient extracted from coarsely powdered seeds of the Poison nut or Quaker buttons plant, commercially available in 20 vol % aqueous ethanolic solutions from Boericke & Tafel; and (vii) *Teucrim marum*—the active ingredient extracted from the entire plant Cat thyme, commercially available in 20 vol % aqueous ethanolic solutions from Boericke & Tafel.

In a preferred formulation, most of the active ingredients are diluted 6× in accordance with the standard homeopathic dilution procedures, with one of the ingredients being diluted 12× and one diluted both 4× and 6×. By "standard homeopathic dilution procedures" is meant that a dilution of 1=1 part by weight active to 9 parts by weight diluent or, in other words, a 10 wt % solution; a 2× dilution=1 part by weight of a 1× solution to 9 parts by weight of diluent dilution, or a 1 wt % solution; a 3× dilution=1 part by weight of a 2× solution to 9 parts by weight of diluent, or a 0.1 wt % solution; and so on. All dilutions may vary with a tolerance of ±10%, preferably ±2%.

Ingredients (i)–(ii) and (iv)–(vii) are preferably diluted 6×, while ingredient (iii) is preferably diluted 12×. In addition to the 6× dilution, ingredient (vi) is also preferably diluted 4×. The solutions of actives may form from about 75 to about 95 wt % of the composition, preferably about 90 wt %. A carrier liquid such as glycerin or other compatible adjuvant may be included in the composition from about 5 to about 15 wt %, preferably about 10 wt %. A preservative may be present in a relatively small amount, say from about 0.05 to about 1 wt %, preferably 0.1 wt %; a preferred preservative is potassium sorbate.

While the composition may be formulated into a wide variety of administration forms such as drops or sprays, the most preferred form is throat spray, as this form has been shown to be effective at quick adsorption into the bloodstream through the mucous membranes of the mouth and throat passageways. The following example demonstrates how to formulate an exemplary embodiment of the invention.

EXAMPLE

The composition of the present invention, comprising 90 wt % solution of active ingredients, 9.9 wt % glycerin diluent/carrier and 0.1 wt % potassium sorbate as a preservative, was formulated as follows. The active ingredient solution portion comprised eight equal parts by weight of ethanol/water solutions made from 20 vol % aqueous ethanolic tinctures of the following homeopathic active ingredients obtained from the commercially available sources mentioned above: (i) Belladonna, (ii) *Ephedra vulgaris*, (iii) *Histamine hydrochloride*, (iv) *Hydrastis canadensis*, (v) *Potassium dichromate*, (vi) *Nux vomica* and (vii) *Teucrim marum*. All ingredients except (iii) were diluted with a mixture of 20 vol % of 95 vol % ethanol in distilled water to form a 0.0001 wt % or 6× solution in accordance with the procedures set forth in the U.S. *Homeopathic Pharmacopeia* (1999) at pages 39–41. Ingredient (iii) was diluted in the same manner to form a $10^{-10}$ wt % or 12× solution. Ingredient (vi) was additionally diluted to form a 0.01 wt % or 4× solution. All eight alcohol/water solutions of actives were combined with the glycerin and potassium sorbate in a mixing vessel and thoroughly mixed with a magnetic stirrer for about 15 minutes to form a solution.

The composition was administered in the form of a throat spray to human subjects suffering from the symptoms of snoring and observed; all showed substantial improvement or elimination of their snoring.

The terms and expressions which have been employed in the forgoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A composition for the relief of the symptoms of snoring comprising an aqueous ethanolic solution of the following components:
   (i) Belladonna;
   (ii) *Ephedra vulgaris;*
   (iii) *Histamine hydrochloride;*
   (iv) *Hydrastis canadensis;*
   (v) *Potassium dichromate;*
   (vi) *Nux vomica;* and
   (vii) *Teucrim marum*
wherein components (i), (ii), (iv), (vi) and (vii) comprise aqueous ethanolic solutions of extracts of the following plants:
   (i) an alkaloid extract of Deadly Nightshade;
   (ii) a decongestant extract of stems and branches of Ma Huang;
   (iv) isoquinoline alkaloid extract of dried rhizome and roots of Golden Seal;
   (vi) extract of seeds of Quaker Buttons; and
   (vii) extract of Cat Thyme.

2. The composition of claim 1 including a carrier.

3. The composition of claim 2 wherein said carrier is glycerin.

4. The composition of claim 1 including a preservative.

5. The composition of claim 4 wherein said preservative is potassium sorbate.

6. The composition of claim 3 wherein glycerin comprises about 9.9 wt % of said composition.

7. The composition of claim 5 wherein potassium sorbate comprises about 0.1 wt % of said composition.

8. A method of treating the symptoms of snoring in a mammal comprising the administration to said mammal an effective amount of the composition of claim 1.

9. The method of claim 8 wherein said mammal is a human.

10. The method of claim 9 wherein said administration is accomplished by the delivery of said solution in the form of a throat spray.

* * * * *